US 6,572,890 B2

(12) United States Patent
Faour et al.

(10) Patent No.: US 6,572,890 B2
(45) Date of Patent: Jun. 3, 2003

(54) OSMOTIC DEVICE CONTAINING VENLAFAXINE AND AN ANTI-PSYCHOTIC AGENT

(75) Inventors: Joaquina Faour, Buenos Aires (AR); Juan Vergez, Buenos Aires (AR)

(73) Assignee: Osmotica Corp., Tortola (VG)

( * ) Notice: Subject to any disclaimer, the term of this patent is extended or adjusted under 35 U.S.C. 154(b) by 0 days.

(21) Appl. No.: 09/728,276

(22) Filed: Nov. 30, 2000

(65) Prior Publication Data

US 2001/0048943 A1 Dec. 6, 2001

Related U.S. Application Data

(60) Provisional application No. 60/175,822, filed on Jan. 13, 2000.

(51) Int. Cl.[7] .............................. A61K 9/24; A61K 9/22; A61K 31/44; A61K 31/41
(52) U.S. Cl. ....................... 424/473; 424/468; 514/220; 514/380
(58) Field of Search ................................ 514/220, 380; 424/468, 473

(56) References Cited

U.S. PATENT DOCUMENTS 4,535,186 A     8/1985   Husbands et al.
6,004,582 A  *  12/1999  Faour et al. ................. 424/473
6,147,072 A  *  11/2000  Bymaster et al. ............ 514/220

FOREIGN PATENT DOCUMENTS

EP          0 830 864 A1      3/1998

OTHER PUBLICATIONS

Physicians Desk Reference "Effexor XR".*
Owen, J. R. And Nemeroff, C.B., New Antidepressants and the Cytochrome $P_{450}$ System: Focus on Venlafaxine, Nefaxodone, and Mirtazapine, Depression and Anxiety, 1198, vol. 7, Supp. 1, 24–32.

* cited by examiner

Primary Examiner—Jose' G. Dees
Assistant Examiner—Robert M DeWitty
(74) Attorney, Agent, or Firm—Rick Matos; Innovar, L.L.C.

(57) ABSTRACT

The present invention provides an osmotic device containing controlled release venlafaxine in the core in combination with an anti-psychotic agent in a rapid release external coat. A wide range of anti-psychotic agents can be used in this device. Particular embodiments of the invention provide osmotic devices having predetermined release profiles. One embodiment of the osmotic device includes an external coat that has been spray-coated rather compression-coated onto the device. The device with spray-coated external core is smaller and easier to swallow than the similar device having a compression-coated external coat. The device is useful for the treatment of depression, anxiety or psychosis related disorders.

23 Claims, 2 Drawing Sheets

OSMOTIC DEVICE CONTAINING VENLAFAXINE AND AN ANTI-PSYCHOTIC AGENT

This application claims benefit of provisional application Ser. No. 60/175,822 filed Jan. 13, 2000.

FIELD OF THE INVENTION

This invention pertains to an osmotic device containing venlafaxine. More particularly, it pertains to an osmotic device tablet that provides a controlled release of venlafaxine, and optionally an anti-psychotic agent, following a particularly advantageous release profile.

BACKGROUND OF THE INVENTION

Clinical depression is a disorder characterized by low self-esteem, guilt, self-reproach, introversion, sadness, despair, sleeping disorders, eating disorders or discouragement. Depression generally causes a lower or decrease of a person's function. Anxiety is a disorder characterized by responses to anticipation of unreal or imagined danger. It manifests itself as increased heart rate, altered respiration rate, sweating, trembling, weakness, or fatigue. Psychosis is a disorder characterized by gross impairment in reality perception as evidenced by delusions, hallucinations, markedly incoherent speech, or disorganized and agitated behavior without apparent awareness on the part of the person of the incomprehensibility of his behavior.

Major depression and anxiety occur concomitantly in more patients than either one alone. When these disorders occur together, they are associated with more severe symptoms, increased impairment of function, a longer chronic course, poorer outcome, and a higher incidence of suicide.

Antidepressants, such as venlafaxine, have been tested for the treatment of depression and symptoms of anxiety. Anti-psychotic agents, such as risperidone, are used for the treatment of psychosis. On occasion, a person suffering from depression or anxiety and psychosis will be prescribed an antidepressant agent and an anti-psychotic agent. Rather than administration of two different dosages, it would be useful in the art to have available a single dosage containing both an antidepressant and an anti-psychotic.

Venlafaxine is commercially available in an extended release capsule dosage form from Wyeth Ayerst under the trademark EFFEXOR XR™. The capsule is available in 37.5, 75, and 150 mg strengths. The capsule is disclosed in U.S. Pat. No. 4,535,186 and does not contain the venlafaxine in combination with an anti-psychotic agent. Moreover, the EFFEXOR XR™ formulation provides an incomplete release of venlafaxine.

Bymaster et al. (European Patent Application No. EP 0830864 A1) disclose a method, and compositions and dosage forms therefor, of treating psychoses with a combination of a serotonin uptake inhibitor and an anti-psychotic agent. Bymaster et al. do not disclose an osmotic device containing such combination nor the beneficial effects of sequential administration of the two drugs, one rapid release and the other controlled release, from a single dosage form.

Controlled release capsule dosage forms and osmotic device dosage forms are generally known by the skilled artisan to provide different release profiles. Effective therapy with antidepressants and anxiolytic agents is dependent upon a careful control of the blood plasma levels of these agents, and therefore, upon the release profiles of these agents from their respective dosage forms.

Osmotic devices and other tablet formulations are known for their ability to provide a controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770, U.S. Pat. No. 6,004,582 to Faour et al., and Argentina Patent No. 199,301, the entire disclosures of which are hereby incorporated by reference.

These references, however, do not disclose osmotic devices that provide the specific plasma profiles or release profiles for venlafaxine (VFX), and an optional anti-psychotic agent, that the present invention provides. Moreover, the prior art does not disclose an osmotic device containing a combination of venlafaxine with an anti-psychotic agent, and generally wherein the venlafaxine and anti-psychotic agent are delivered according to specific release profiles that are advantageous over known formulations.

SUMMARY OF THE INVENTION

In one aspect, the present invention provides an osmotic device comprising:
- a core comprising a therapeutically effective amount of venlafaxine and at least one osmotic agent or osmopolymer; and
- a semipermeable membrane surrounding the core and having a passageway there through;
- wherein the core provides a controlled release of VFX, and at least 80% of the VFX is released within 13 hours after exposure of the osmotic device to an aqueous solution.

Another aspect of the present invention provides an osmotic device for the delivery of VFX and an anti-psychotic agent comprising:
- a core comprising a therapeutically effective amount of venlafaxine and at least one osmotic agent or osmopolymer;
- a semipermeable membrane surrounding the core and having a passageway there through; and
- an external coat comprising a therapeutically effective amount of an anti-psychotic agent;
- wherein the core provides a controlled release of VFX, and at least 80% of the VFX is released within 13 hours after exposure of the osmotic device to an aqueous solution, and the external coat provides a rapid release of the anti-psychotic agent, and at least 75% of the anti-psychotic agent is released within 1 hour after exposure of the osmotic device to an aqueous solution.

In some embodiments, the external coat is applied by spray coating or compression coating. By spray coating rather than compression coating the external coat, a thinner external coat, and therefore a smaller osmotic device, is formed.

Another aspect of the invention provides a method of treating depression, anxiety and/or psychosis in a mammal, the method comprising the step of administering an osmotic device which provides a controlled release of VFX from its core and a rapid release of an anti-psychotic agent from an external coat, wherein at least 75% of the anti-psychotic agent is released within about 40 minutes, and at least about 60% of the VFX is released within about 12 hours after administration.

Figure 1:
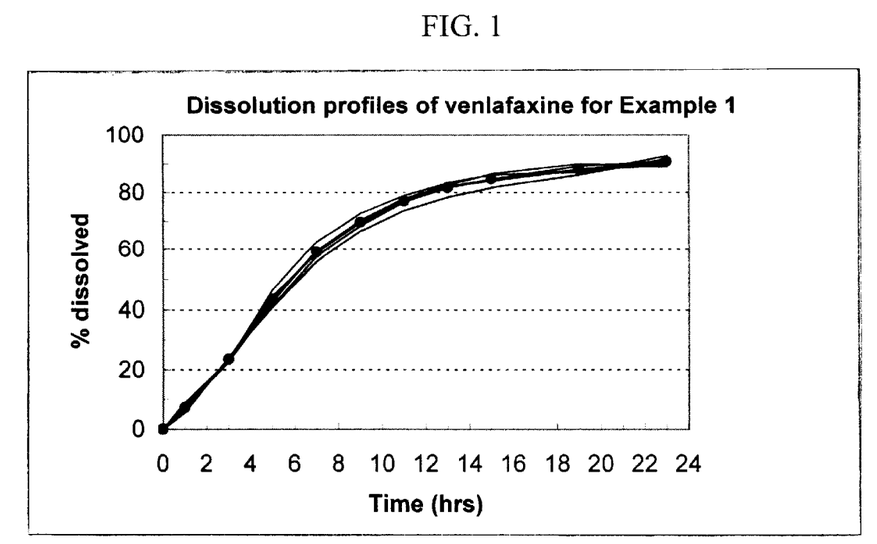
FIG. 1 depicts an in vitro release profile for VFX from the exemplary formulation of Example 1.
Figure 2:
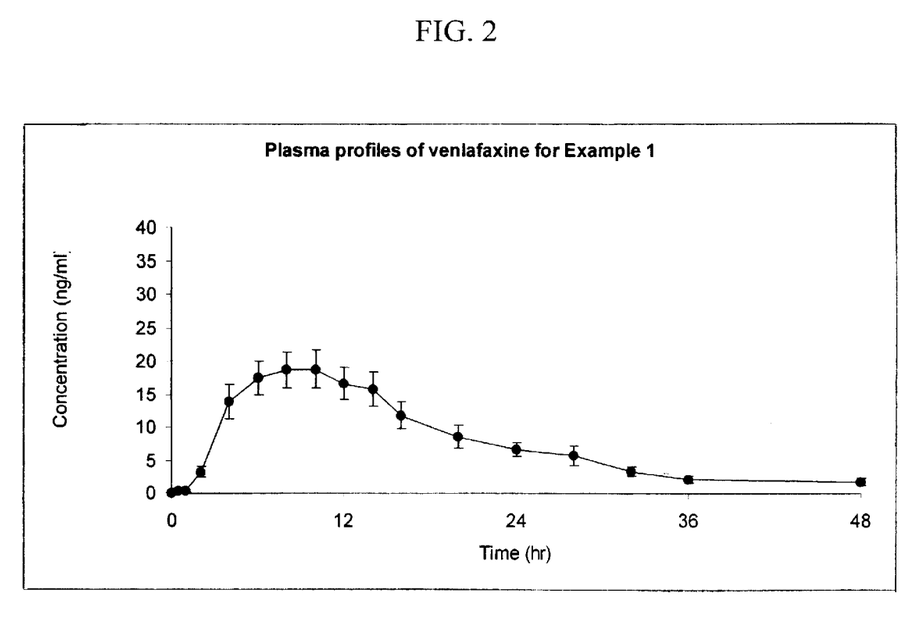
FIG. 2 depicts an in vivo plasma profile for VFX from the exemplary formulation of Example 1.
Figure 4:
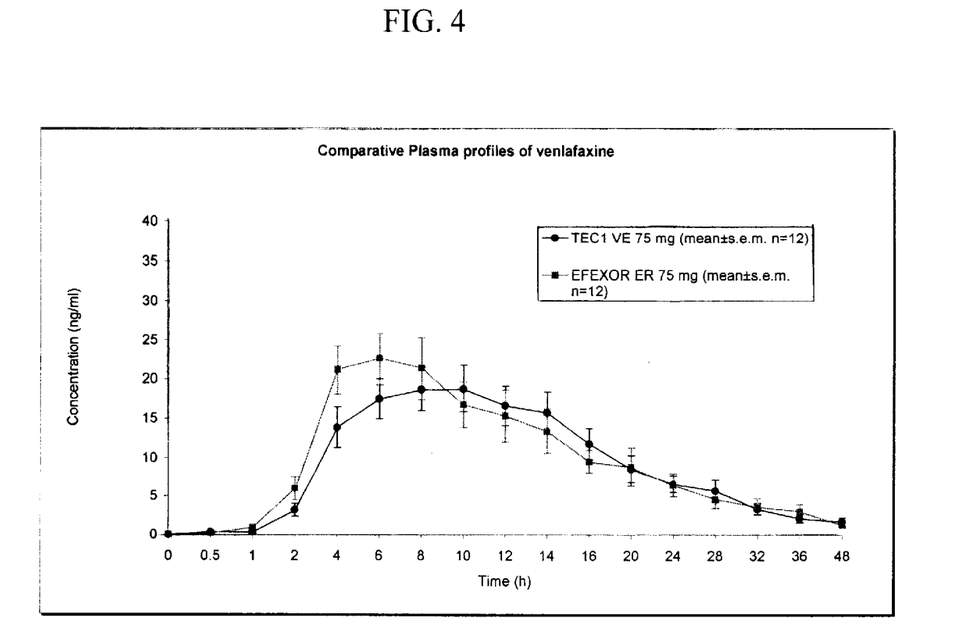
FIG. 4 depicts a comparative plot including the plasma profiles of FIGS. 2 and 3.

In other embodiments, the osmotic device provides: a) a VFX release profile similar to that shown in FIG. 1; or b) a VFX plasma profile similar to that shown in FIGS. 2 or 4. In still other embodiments, the release of VFX and/or the anti-psychotic agent has a delayed onset.

In even other embodiments, the anti-psychotic agent is selected from the group consisting of risperidone, olanzapine, clozapine, sertindole, ziprasidone, quetiapine, sulpiride, pimozide, clothiapine, molindone, loxapine, trifluoperazine, haloperidol, flupenthixol, chlorpromazine, chlorprothixene, clopenthixol, droperidol, perphenazine, fluphenazine, lithium, mesoridazine, spiperone, promazine, prochlorperazine, thioridazine, thiothixene, triflupromazine, and raclopride.

In yet other embodiments, the following anti-psychotic agents are administered in the indicated doses: a) risperidone—5 to 10 mg per day; b) olanzapine—5 to 20 mg, 0.25–50 mg, 1–30 mg, or 1–25 mg per day; c) clozapine—100 to 400 mg, 12.5–900 mg, or 150–450 mg per day; d) sertindole—15 to 20 mg per day or 0.0001 to 1.0 mg/kg of body weight per day; e) ziprasidone—80 to 160 mg, 5 to 500 mg or 50 to 100 mg per day; f) quetiapine—150 to 600 mg or 1.0–40 mg/kg of body weight per day; g) sulpiride—50 to 100 mg per day; h) pimozide—2 to 4 mg per day; or i) clothiapine—40 mg per day.

The venlafaxine, as either its free base or salt form, will be administered once daily in doses ranging form about 10 to 150 mg, 25 to 125 mg, 150 to 300 mg, or 10–500 mg.

The osmotic device generally delivers the anti-psychotic agent to the upper GI tract and the venlafaxine to the middle to lower GI tract.

Other features, advantages and embodiments of the invention will become apparent to those skilled in the art by the following description, accompanying examples.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Venlafaxine and anti-psychotic agents are available from a large number of commercial sources. The invention provides for the administration of venlafaxine alone or in combination with an anti-psychotic agent, wherein these compounds are in their free base, free acid, racemic, optically pure, diastereomeric and/or pharmaceutically acceptable salt forms.

As used herein, "pharmaceutically acceptable salts" refer to derivatives of the disclosed compounds wherein the therapeutic compound is modified by making acid or base salts thereof. Examples of pharmaceutically acceptable salts include, but are not limited to, mineral or organic acid salts of the VFX or anti-psychotic agent. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfuric, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

FIG. 1 depicts various venlafaxine in vitro release profiles for the osmotic device tablets described in Example 1 (average of 6 runs). This formulation exhibits a 22-hour or greater controlled release of VFX. The VFX release profile of this exemplary formulation is generally described as follows:

| Time (h) | Maximum Percent Released | Minimum Percent Released |
| --- | --- | --- |
| 1 | 9.0 | 5.6 |
| 3 | 24.1 | 22.8 |
| 5 | 46.6 | 41.0 |
| 7 | 62.7 | 55.9 |
| 9 | 72.9 | 66.6 |
| 11 | 79.0 | 73.9 |
| 13 | 83.4 | 78.6 |
| 15 | 86.6 | 81.8 |
| 19 | 90.1 | 86.3 |
| 23 | ≧92.9 | 89.0 |

The venlafaxine release profile can also be described as follows:

| Time (h) | Released (%) | STD (%) |
| --- | --- | --- |
| 1 | 7.2 | 1.3 |
| 3 | 23.6 | 0.5 |
| 5 | 43.3 | 2.1 |
| 7 | 59.0 | 2.3 |
| 9 | 69.7 | 2.1 |
| 11 | 77.0 | 1.8 |
| 13 | 81.8 | 1.7 |
| 15 | 84.7 | 1.7 |
| 19 | 88.1 | 1.4 |
| 23 | ≧90.8 | 1.5 |

FIG. 2. Depicts an VFX in vivo plasma profile for the osmotic device tablets described in Example 1 (mean±S.D., n=12 runs). This exemplary device provides therapeutically effective levels of VFX between the period of about 1 to about 36 hours after administration. Therapeutic VFX plasma concentration levels range from about 2 to about 37 ng/ml, generally about 2 to about 22 ng/ml. The mean $C_{max}$ is about 19 ng of VFX per ml of plasma at about 8–10 hours after administration. The in vivo plasma profile can be characterized as follows:

| Time after Administration (h) | Mean VFX Plasma Concentration (ng/ml) | S.E.M. |
|---|---|---|
| 0 | 0.0 | 0.0 |
| 0.5 | 0.3 | 0.2 |
| 1 | 0.4 | 0.2 |
| 2 | 3.2 | 0.8 |
| 4 | 13.9 | 2.6 |
| 6 | 17.5 | 2.5 |
| 8 | 18.7 | 2.7 |
| 10 | 18.8 | 2.9 |

| Time after Administration (h) | Mean VFX Plasma Concentration (ng/ml) | S.E.M. |
|---|---|---|
| 12 | 16.7 | 2.5 |
| 14 | 15.8 | 2.7 |
| 16 | 11.8 | 2.0 |
| 20 | 8.6 | 1.7 |
| 24 | 6.6 | 1.1 |
| 28 | 5.7 | 1.5 |
| 32 | 3.4 | 0.7 |
| 36 | 2.2 | 0.5 |
| 48 | 1.7 | 0.5 |

SD denotes "standard deviation".

The osmotic device generally provides the above-described plasma profile after administration of a single daily dose, i.e. acute dosing. The artisan of ordinary skill will understand that chronic daily dosing of the osmotic device will generally result in a relatively flat plasma profile over a 24-hour period for venlafaxine and optionally the anti-psychotic agent, since a steady-state or equilibrium will be reached due to chronic administration.

Figure 3:
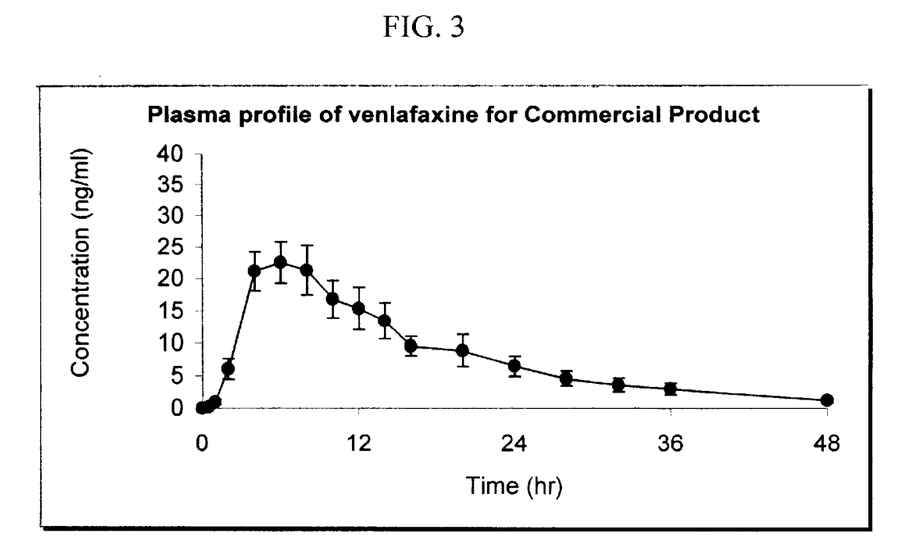
FIG. 3 depicts an in vivo plasma profile for the commercial product EFFEXOR ER.

FIG. 3. depicts an VFX in vivo plasma profile for the EFFEXOR ER 75 mg product (mean±S.D., n=12). The mean $C_{max}$ for the commercial product is about 23 ng of VFX per ml of plasma at about 8–10 hours after administration. FIG. 5 depicts comparative data for the in vivo VFX of the formulations of the invention and of the commercial product. The data shows absolute differences in the $C_{max}$ and $T_{max}$ values achieved.

All of the tablet formulations of the invention will provide therapeutically effective levels of venlafaxine and an anti-psychotic agent for at least a predetermined period of time. The tablets of the invention will generally provide therapeutically effective amounts of venlafaxine for a total time period of not less than 18 hours and not more than 30 hours, generally not less than 20 hours and not more than 24 hours, or not less than 22 hours.

The external coating can be an immediately dissolving coating that dissolves in the buccal cavity or a rapidly dissolving coating that dissolved in the stomach, jejunum or duodenum. The controlled release core generally begins to release venlafaxine within about 2 hours after administration.

The rapid release coating will release all of its anti-psychotic agent within three hours after administration and preferably at least 75% of its anti-psychotic agent within about 40 minutes after administration. While the anti-psychotic agent is released over a short period of time, the therapeutic benefit that it provides will last at least 12 hours and generally up to about 24 hours. The actual time period will vary according to the anti-psychotic agent used and, in particular, its half-life in a patient.

Those of ordinary skill in the art will appreciate that the particular amounts of venlafaxine and anti-psychotic agent used in the osmotic device will vary according to, among other things, the desired pharmacokinetic behavior in a mammal.

When a rapidly dissolving coat is used in the tablet formulations of the invention, the coat will generally comprise an inert and non-toxic material that is at least partially, and generally substantially completely, soluble or erodible in an environment of use. The rapidly dissolving coat will be soluble in the buccal cavity and/or upper GI tract, such as the stomach, duodenum, jejunum or upper small intestines. Exemplary materials are disclosed in U.S. Pat. Nos. 4,576,604 and 4,673,405, and the text Pharmaceutical Dosage Forms: Tablets Volume I, Second Edition. A. Lieberman. ed. 1989, Marcel Dekker, Inc. the relevant disclosures of which are hereby incorporated by reference. In embodiments, the rapidly dissolving coat will be soluble in saliva, gastric juices, or acidic fluids.

The long acting controlled release tablet formulations that provide a delayed and sustained release of venlafaxine may

| | Calculated PK parameters | | Bioequivalence evaluation | | |
|---|---|---|---|---|---|
| Parameter | Example 1 (75 mg) | REF (EFFEXOR ® ER 75 mg) | Geometric mean Relative bioavailability % | 90% Confidence Interval | Bioequivalence Limits |
| ABC∞ (ng.h/ml) | 388.8 ± 64.4 | 398.5 ± 71.6 | 99.4 | 92.2–102.9 | 80–120 |
| $C_{max}$ (ng/ml) | 20.4 ± 2.8 | 23.4 ± 3.3 | 87.8 | 81.9–92.9 | 80–120 |
| $C_{max}$/ABC∞ | 0.057 ± 0.004 | 0.064 ± 0.005 | 88.5 | 82.8–93.2 | 80–120 |
| $t_{max}$ (h) | 9.0 ± 2.0 | 6.0 ± 2.5 | — | — | — |
| Ke (h$^{-1}$) | 0.077 ± 0.007 | 0.079 ± 0.010 | — | — | — |

The release profile of the osmotic device of the invention is preferred as it provides a lower $C_{max}$ and longer $T_{max}$ while at the same time maintaining therapeutically effective levels thereof over an extended period of time.

Depending upon the particular combination of ingredients used to prepare the osmotic device, it will generally provide an expected overall venlafaxine release profile resembling a pseudo-first order, first-order, pseudo-second order, second order, pseudo-third order or third order release profile.

include an enteric coat that is soluble or erodible in intestinal juices, substantially pH neutral or basic fluids but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimellitate (CAT), poly(vinyl acetate) phthalate (PVAP), hydroxypropyl methylcellulose phthalate (HP), poly(methacrylate ethylacrylate) (1:1) copolymer (MA-EA), poly(methacrylate methylmethacrylate) (1:1) copolymer (MA-MMA), poly (methacrylate methylmethacrylate) (1:2) copolymer, Eudragit L-30-D™ (MA-EA, 1:1), Eudragit™ L-100-55™ (MA-EA, 1:1), hydroxypropyl methylcellulose acetate succinate (HPMCAS), Coateric™ (PVAP), Aquateric™ (CAP), AQUACOAT™ (HPMCAS) and combinations thereof The enteric coat can also comprise dissolution aids, stability modifiers, and bioabsorption enhancers.

When the enteric coat is intended to be dissolved, eroded or become detached from the core in the colon, materials such as hydroxypropylcellulose, microcrystalline cellulose (MCC, Avicel™ from FMC Corp.), poly (ethylene—vinyl acetate) (60:40) copolymer (EVAC from Aldrich Chemical Co.), 2-hydroxyethylmethacrylate (HEMA), MMA, terpolymers of HEMA: MMA:MA synthesized in the presence of N,N'-bis(methacryloyloxyethyloxycarbonylamino)— azobenzene, azopolymers, enteric coated timed release system (Time Clock® from Pharmaceutical Profiles, Ltd., UK) and calcium pectinate can be used.

A polymeric material for use in the enteric coat involves enteric materials that resist the action of gastric fluid avoiding permeation through the semipermeable wall while one or more of the materials in the core of the tablet are solubilized in the intestinal tract thereby allowing delivery of the venlafaxine in the core by osmotic pumping in an osmotic device to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The enteric coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsam of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methylmethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropyl methylcellulose phthalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

The semipermeable membrane of the osmotic device is formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose ethers and cellulose esters-ethers. However, it has been found that a semipermeable membrane consisting essentially of cellulose acetate (CA) and poly(ethylene glycol) (PEG), in particular PEG 400, are when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and generally about 95% by weight of CA: about 5% by weight of PEG. The ratio can be varied to alter permeability and ultimately the release profile of the osmotic device. Other materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core of the osmotic device tablet of the present invention will comprise venlafaxine, at least one pharmaceutically acceptable excipient and optionally one or more other materials. Generally, the tablet formulations will comprise about 0.1–99.9% by weight of venlafaxine in the uncoated tablet core. Ranges will vary according to the anti-psychotic agent used and the intended use of the osmotic device.

When the controlled release tablet is an osmotic device, osmotically effective solutes, osmotic agents or osmagents are added. These osmagents can aid in either the suspension or dissolution of the VFX in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of VFX therefrom.

The tablets of the invention can also comprise an acidifying agent, alkalizing agent, adsorbent, antioxidant, buffering agent, colorant, flavorant, sweetening agent, tablet antiadherent, tablet binder, tablet and capsule diluent, tablet direct compression excipient, tablet disintegrant, tablet glidant, tablet lubricant, tablet or capsule opaquant and/or tablet polishing agents.

As used herein, the term "adsorbent" is intended to mean an agent capable of holding other molecules onto its surface by physical or chemical (chemisorption) means. Such compounds include, by way of example and without limitation, powdered and activated charcoal and other materials known to one of ordinary skill in the art.

As used herein, the term "antioxidant" is intended to mean an agent that inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "alkalizing agent" is intended to mean a compound used to provide alkaline medium for product stability. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art.

As used herein, the term "acidifying agent" is intended to mean a compound used to provide an acidic medium for product stability. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, aspartame, dextrose, glycerin, mannitol, saccharin sodium, sorbitol and sucrose and other materials known to one of ordinary skill in the art.

As used herein, the term "tablet antiadherent" is intended to mean an agent which prevent the sticking of tablet formulation ingredients to punches and dies in a tableting machine during production. Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binder" is intended to mean a substance used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "filler" is intended to mean inert substances used as fillers to create the desired bulk, flow properties, and compression characteristics in the preparation of tablets and capsules. Such compounds include, by way of example and without limitation, dibasic calcium phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose (e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, red, other F.D. & C. dyes and natural coloring agents such as grape skin extract, beet red powder, beta-carotene, annato, carmine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend-on a number of factors, including the organoleptic effect desired. Flavors will be present in any amount as desired by those of ordinary skill in the art. Particular flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly (ethylene glycol) Chemistry: Biotechnical and Biomedical Applications (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glycerides and acetylated fatty acid glycerides. It can also be mixed with alcohols, such as ethanol, isopropanol, hexadecyl alcohol, glycerol and propylene glycol; with glycerol ketals, such as 2,2-dimethyl-1,3-dioxolane-4-methanol; with ethers, such as poly(ethyleneglycol) 450, with petroleum hydrocarbons, such as mineral oil and petrolatum; with water, or with mixtures thereof with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene—maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of venlafaxine which is sufficient to elicit the required or desired therapeutic response, or in other words, the amount which is sufficient to elicit an appreciable biological response when administered to a patient.

The tablets (osmotic devices) of the invention can assume any shape or form known in the art of pharmaceutical sciences. The device of the invention can be a pill, sphere, tablet, bar, plate, paraboloid of revolution, ellipsoid of revolution or the like. The tablets can also include surface markings, cuttings, grooves, letters and/or numerals for the purposes of decoration, identification and/or other purposes.

The tablets (osmotic devices) of the invention can be prepared according to the methods disclosed herein or those well known in the art, more specifically according to the methods disclosed in the disclosure incorporated herein by reference. For example, according to one manufacturing technique, venlafaxine and excipients that comprise the core are mixed in solid, semisolid or gelatinous form, then moistened and sieved through a specified screen to obtain uncoated cores. The uncoated cores are then dried in a dryer and compressed, for example, by punching. The compressed and uncoated cores are then covered with a semipermeable membrane. Subsequently, the semipermeable membrane surrounding the core should be perforated with, for example, laser equipment. Finally, an external coat containing the anti-psychotic agent is applied to the semipermeable membrane.

The external coat can be applied as a compression coating, but it is generally applied as a sprayed coating. The sprayed coating is thinner and lighter than the compression coating, and an osmotic device including the sprayed on external coating is, therefore, smaller than a similar osmotic device having a compression coat. A smaller size osmotic device generally results in increased patient compliance in taking the osmotic device and is therefore advantageous.

The tablets (osmotic devices) of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The osmotic device of the invention comprises at least one passageway (pore, hole, or aperture) which communicates the exterior of the semipermeable wall with the core of the device. The passageway can be formed according to any of the known methods of forming passageways in a semipermeable membrane. Such methods include, for example, 1) drilling a hole through the semipermeable membrane with a bit or laser; 2) including a water soluble material within the composition that forms the semipermeable membrane such that a pore forms when the osmotic device is in an aqueous environment of use; 3) punching a hole through the semipermeable membrane; or 4) employing a tablet punch having a pin to punch a hole through the semipermeable lamina. The passageway can pass through the semipermeable wall and one or more of any other lamina coated onto the semipermeable membrane or between the semipermeable membrane and the core. The passageway(s) can be shaped as desired. In some embodiments, the passageway is laser drilled and is shaped as an oval, ellipse, slot, slit, cross or circle.

Methods of forming passageways in semipermeable membranes of osmotic devices are disclosed in U.S. Pat. No. 4,088,864 to Theeuwes et al., U.S. Pat. No. 4,016,880 to Theeuwes et al., U.S. Pat. No. 3,916,899 to Theeuwes et al., U.S. Pat. No. 4,285,987 to Ayer et al., U.S. Pat. No. 4,783,337 to Wong et al., U.S. Pat. No. 5,558,879 to Chen et al., U.S. Pat. No. 4,801,461 to Hamel et al., and U.S. Pat. No. 3,845,770 to Theeuwes et al., the disclosures of which are hereby incorporated by reference.

The preformed passageway, e.g., one made by mechanical means, is formed after the semipermeable membrane is applied to the core. It can be formed either before or after the inert water soluble coat and/or drug-containing external coat is applied to the semipermeable membrane.

The advantages of the present system over known systems for administering venlafaxine in combination with an anti-psychotic agent is improved therapeutic benefit, simplified manufacturing, and increased patient compliance. Moreover, the present formulation will provide an enhanced therapeutic effect when compared to the administration of venlafaxine alone.

By administration of the venlafaxine in a controlled release fashion and the anti-psychotic agent in a rapid release fashion, the osmotic device unexpectedly provides an improved pharmacological profile including reduced side effects, lower drug requirement and/or enhanced therapeutic benefit as compared to other known methods or dosage forms.

The osmotic device of the invention is useful for treating a variety of psychological disorders. The osmotic device can be used to treat psychotic conditions and mild anxiety with the atypical anti-psychotics without the concomitant weight gain typically observed with such treatment, conferring a marked and unexpected benefit on the patient. The present invention furthermore provides a potentiation of the increase in the concentration of norepinephrine observed as an effect of administration of a first component compound, by administration of a second component compound.

The present invention is particularly suited for use in the treatment of bipolar disorders, mania (mixed state), schizoaffective disorders characterized by the occurrence of a depressive episode during the period of illness, and depression with psychotic features. Such disorders may often be resistant to treatment with an anti-psychotic alone.

The present invention is also useful for the treatment of premenstrual syndrome (PMS) and anorexia nervosa. Furthermore, the present invention is useful for the treatment of the agression/violence which may be associated with certain disorders. These disorders include, but are not limited to, mania, schizophrenia, schizoaffective disorders, substance abuse, head injury, and mental retardation.

Psychotic conditions to be treated by the present osmotic device include, for example, schizophrenia, schizophreniform diseases, acute mania, schizoaffective disorders, and depression with psychotic features. The titles given these conditions represent multiple disease states. The following list illustrates a number of these disease states, many of which are classified in the Diagnostic and Statistical Manual of Mental Disorders, 4th Edition, published by the American Psychiatric Association (DSM). The DSM code numbers for these disease states are supplied below, when available, for the convenience of the reader: Paranoid Type Schizophrenia 295.30; Disorganized Type Schizophrenia 295.10; Catatonic Type Schizophrenia 295.20; Undifferentiated Type Schizophrenia 295.90; Residual Type Schizophrenia 295.60; Schizophreniform Disorder 295.40; Schizoaffective Disorder 295.70; Schizoaffective Disorder of the Depressive Type; and Major Depressive Disorder with Psychotic Features 296.24, 296.34.

Psychoses are often associated with other diseases and conditions, or caused by such other conditions. For example, they are associated with neurological conditions, endocrine conditions, metabolic conditions, fluid or electrolyte imbalances, hepatic or renal diseases, and autoimmune disorders with central nervous system involvement. Psychoses may also be associated with use or abuse of certain substances. These substances include, but are not limited to cocaine, methylphenidate, dexamethasone, amphetamine and related substances, cannabis, hallucinogens, inhalants, opioids, phencyclidine, sedatives, hypnotics and anxiolytics. Psychotic disorders may also occur in association with withdrawal from certain substances. These substances include, but are not limited to, sedatives, hypnotics and anxiolytics. The embodiments of the present invention are useful for treatment of psychotic conditions associated with any of these conditions.

The following examples should not be considered exhaustive, but merely illustrative of only a few of the many embodiments contemplated by the present invention. The methods described herein can be followed to prepare osmotic devices according to the invention.

EXAMPLE 1

A scale batch of Venlafaxine HCl 75 mg was prepared by mixing 84.86 g of Venlafaxine HCl, 238.83 g of Mannitol and 25.0 g of Povidone. The mixture was wetting with a blend of 120.00 ml of alcohol 960, 22.31 g of Polyethylene Glycol 6000 and 1.50 g of Polyethylene Glycol 400. The blend was granulated and dried at 40–50° C. for 3 hours; then, it was screened and mixed with 3.00 g of Colloidal Silicon Dioxide. The blend was mixed to homogenize and 4.50 g of Magnesium Stearate was added as lubricant. The final blend was tabletted using biconcaves, 9.25-mm diameter punches. Cores weight: 380.0 mg. Hardness from 7 to 12 kp.

A first composition to cover the cores was prepared as follows: 7.53 g of Copolyvidone, 10,50 g of hydroxypropyl methylcellulose 2910, 3.00 g of Polyethylene Glycol 6000 and 3.97 g of Titanium Dioxide in Isopropyl Alcohol.

This polymer mixture was sprayed onto the tablets in a conventional pan coater to obtain film-coated tablets whose membrane coating weighed 25 mg approximately. A second composition to cover the film-coated tablets was prepared as follows: 27.93 g of Cellulose Acetate and 1.47 g of Polyethylene Glycol 400 in a mixture of 495.0 ml of Methylene Chloride and 125.0 ml of Methyl Alcohol. This polymer mixture was sprayed onto the tablets in a conventional pan coater to obtain film-coated tablets whose membrane coating weighed 29.4 mg approximately. A 0.50-mm hole was drilled through the coating in one face of the tablet.

The final coating was prepared by mixing 9,45 g of hydroxypropyl methylcellulose 2910, 6.78 g of Copolyvidone, 2.70 g of Polyethylene Glycol 6000, 3.20 g of Titanium Dioxide, 90.00 mg of Aluminum Lake Quinoline Yellow and 5.40 mg of Aluminum Lake Sunset Yellow in a mixture of Methylene Chloride-Alcohol 96° 70:30 v/v (volume/volume). This polymer mixture was sprayed onto the tablets in a conventional pan coater to obtain film-coated tablets whose membrane coating weighed 15 mg approximately.

Tablets made according to the above procedure will generally have the following composition.

| INGREDIENT | 37.5 mg | 75 mg | 150 mg |
| --- | --- | --- | --- |
| CORE | | | |
| Venlafaxine Hydrochloride | 42.430 mg | 84.860 mg | 169.720 mg |
| Mannitol | 119.415 mg | 238.830 mg | 477.660 mg |
| Povidone | 12.500 mg | 25.00 mg | 50.000 mg |
| Polyethylene Glycol 400 | 0.750 mg | 1.500 mg | 3.000 mg |
| Colloidal Silicon Dioxide | 1.500 mg | 3.000 mg | 6.000 mg |
| Polyethylene Glycol 6000 | 11.155 mg | 22.310 mg | 44.620 mg |
| Magnesium Stearate | 2.250 mg | 4.500 mg | 9.000 mg |
| COATING A | | | |
| Copolyvidone | 5.420 mg | 7.530 mg | 11.930 mg |
| Hydroxypropyl methylcellulose 2910 | 7.560 mg | 10.500 mg | 16.630 mg |
| Polyethylene Glycol 6000 | 2.160 mg | 3.000 mg | 4.750 mg |
| Titanium Dioxide | 2.860 mg | 3.970 mg | 6.290 mg |
| COATING B | | | |
| Cellulose Acetate | 23.040 mg | 27.930 mg | 60.440 mg |
| Polyethylene Glycol 400 | 1.210 mg | 1.470 mg | 4.130 mg |
| COATING C | | | |
| Hydroxypropyl methylcellulose 2910 | 3.150 mg | 6.300 mg | 10.080 mg |
| Copolyvidone | 2.260 mg | 4.520 mg | 7.230 mg |
| Polyethylene Glycol 6000 | 0.900 mg | 1.800 mg | 2.880 mg |
| Titanium Dioxide | 1.158 mg | 2.136 mg | 3.709 mg |
| Aluminum Lake Quinoline Yellow | 0.030 mg | 0.060 mg | 0.095 mg |
| Aluminum Lake Sunset Yellow | 0.0018 mg | 0.0036 mg | 0.0060 mg |

EXAMPLE 2

A large scale batch of venlafaxine and risperidone containing tablets was prepared by mixing 84.86 g of Venlafaxine HCl, 238.83 g of Mannitol and 25.0 g of Povidone. The mixture was wetting with a blend of 120.00 ml of alcohol 960, 22.31 g of Polyethylene Glycol 6000 and 1.50 g of Polyethylene Glycol 400. The blend was granulated and dried at 40–50° C. for 3 hours; then, it was screened and mixed with 3.00 g of Colloidal Silicon Dioxide. The blend was mixed to homogenize and 4.50 g of Magnesium Stearate was added as lubricant. The final blend was tabletted using biconcaves, 9.25-mm diameter punches. Cores weight: 380.0 mg. Hardness from 7 to 12 kp.

A first composition to cover the cores was prepared as follows: 7.53 g of Copolyvidone, 10,50 g of hydroxypropyl methylcellulose 2910, 3.00 g of Polyethylene Glycol 6000 and 3.97 g of Titanium Dioxide in Isopropyl Alcohol. This polymer mixture was sprayed onto the tablets in a conventional pan coater to obtain film-coated tablets whose membrane coating weighed 25 mg approximately.

A second composition to cover the film-coated tablets was prepared as follows: 27.93 g of Cellulose Acetate and 1.47 g of Polyethylene Glycol 400 in a mixture of 495 ml of Methylene Chloride and 125 ml of Methyl Alcohol. This polymer mixture was sprayed onto the tablets in a conventional pan coater to obtain film-coated tablets whose membrane coating weighed 29.4 mg approximately. A 0.50-mm hole was drilled through the coating in one face of the tablet.

The third composition was prepared by mixing 4.39 g of Copolyvidone, 3.94 g of Titanium Dioxide, 14.17 g of Talc and 9,00 mg of Aluminum Lake Brilliant Blue in Isopropyl Alcohol.

This polymer mixture was sprayed onto the tablets in a conventional pan coater to obtain film-coated tablets whose membrane coating weighed 15 mg approximately.

The rapid release external coating was prepared by mixing 5.00 g of Risperidone, 381.00 g of Microcrystalline Cellulose, 32.00 g of Povidone, 20.50 g of Crospovidone and 3.00 g of Colloidal Silicon Dioxide. The mixture was blended to homogenize; then, 8.50 g of Magnesium Stearate was added as lubricant. This blend was tabletted to over the film-coated tablets by compression using biconcaves, 14.0-mm diameter punches. Coating weight: 450 mg. Hardness from 8 to 12 kp.

The final coating was prepared by mixing 22,68 g of Hydroxypropyl methylcellulose 2910, 6.47 g of Polyethylene Glycol 6000, 8.31 g of Titanium Dioxide and 45.00 mg of Aluminum Lake Red Ponceau in a mixture of Methylene Chloride-Alcohol 96° 70:30 v/v (volume/volume). This polymer mixture was sprayed onto the tablets in a conventional pan coater to obtain film-coated tablets whose membrane coating weighed 25 mg approximately.

Tablets made according to the above procedure generally have the following formulation.

| CORE | |
| --- | --- |
| Venlafaxine Hydrochloride | 84.860 mg |
| Mannitol | 238.830 mg |
| Povidone | 25.00 mg |
| Polyethylene Glycol 400 | 1.500 mg |
| Colloidal Silicon Dioxide | 3.000 mg |
| Polyethylene Glycol 6000 | 22.310 mg |
| Magnesium Stearate | 4.500 mg |
| COATING A | |
| Copolyvidone | 7.530 mg |
| Hydroxypropyl methylcellulose 2910 | 10.500 mg |
| Polyethylene Glycol 6000 | 3.000 mg |
| Titanium Dioxide | 3.970 mg |

-continued

| COATING B | |
| --- | --- |
| Cellulose Acetate | 27.930 mg |
| Polyethylene Glycol 400 | 1.470 mg |
| COATING C | |
| Copolyvidone | 2.925 mg |
| Titanium Dioxide | 2.625 mg |
| Talc | 9.444 mg |
| Aluminum Lake Brillant Blue | 0.006 mg |
| COATING D | |
| Risperidone | 5.000 mg |
| Microcrystalline Cellulose | 381.000 mg |
| Povidone | 32.000 mg |
| Crospovidone | 20.500 mg |
| Colloidal Silicon Dioxide | 3.000 mg |
| Magnesium Stearate | 8.500 mg |
| COATING E | |
| Hydroxypropyl methylcellulose 2910 | 15.120 mg |
| Polyethylene Glycol 6000 | 4.310 mg |
| Titanium Dioxide | 5.540 mg |
| Aluminum Lake Red Ponceau | 0.030 mg |

EXAMPLE 3

The following general method was used to administer the osmotic device of the invention to human patients and to evaluate the performance of the osmotic device of the invention to that of the EFFEXOR XR capsule. The bioavailability of the osmotic device was evaluated using a two-period, single-dose, cross-over randomized pharmacokinetic study with a one-week washout period using EFFEXOR XR as the control product. Twelve healthy hospitalized subjects (non-smokers between the ages of 21–50) were randomly separated into two equally sized groups. The first group received the formulation of Example 1 (75 mg of venlafaxine) and the second group received the control formulation thirty minutes after a normal breakfast during the first period. After the washout period, the first group received the control formulation and the second group received the formulation of Example 1 during a second period. Blood samples were taken periodically from 0 to 48 hrs after administration and plasma aliquots were obtained immediately and stored at −20° C. for later analysis by HPLC to determine VFX content. The following pharmacokinetic parameters were calculated from the plasma concentration curve for each formulation and each subject: area under the curve from 0–48 hrs ($AUC_{0-t}$) and extrapolated to infinity ($AUC_{0-inf}$); maximum concentration of VFX in plasma ($C_{max}$); and time to reach $C_{max}$ ($T_{max}$). Safety was evaluated by physical examination, vital signs and adverse event records. Statistical comparisons were made using Analysis of Variance (ANOVA) for the crossover design. Geometric means and classical 90% confidence intervals for the ratio (test/control) of means were calculated in order to evaluate bioequivalence.

EXAMPLE 4

The following general formulation was used to make an osmotic device according to Example 1, which has a dissolution profile similar to that depicted in FIG. 1 and provides a plasma profile similar to that depicted in FIG. 2.

| INGREDIENT | Amount (mg) |
|---|---|
| CORE | |
| Venlafaxine (salt or free form) | 10–500 |
| Osmagent | 350–500 |
| Binder | 15–100 |
| Plasticizer (lower molecular weight) | 0.1–50 |
| Glidant | 0.1–12 |
| Plasticizer (higher molecular weight) | 5–60 |
| Lubricant | 2–15 |
| COATING A | |
| First water soluble polymer | 8–15 |
| Second water soluble polymer | 5–25 |
| Plasticizer (higher molecular weight) | 0.2–4 |
| Opaquant | 0.1–12 |
| COATING B | |
| Cellulose ester | 40–75 |
| Plasticizer (lower molecular weight) | 0.5–13 |
| COATING C | |
| Second water soluble polymer | 5–30 |
| Third water soluble polymer | 3–15 |
| Plasticizer (higher molecular weight) | 1–6 |
| Opaquant | 2–8 |
| First Colorant | 0.01–0.1 |
| Second Colorant | 0.001–0.05 |

EXAMPLE 5

The following general formulation was used to make an osmotic device according to Example 2, which has a dissolution profile similar to that depicted FIG. 1 and provides a plasma profile similar to that depicted in FIG. 2.

| INGREDIENT | Amount (mg) |
|---|---|
| CORE | |
| Venlafaxine (salt or free form) | 10–500 |
| Osmagent | 175–250 |
| Binder | 7.5–50 |
| Plasticizer (lower molecular weight) | 0.1–25 |
| Glidant | 0.1–6 |
| Plasticizer (higher molecular weight) | 2.5–30 |
| Lubricant | 1–7.5 |
| COATING A | |
| First water soluble polymer | 4–7.5 |
| Second water soluble polymer | 2.5–12.5 |
| Plasticizer (higher molecular weight) | 0.1–2 |
| Opaquant | 0.1–6 |
| COATING B | |
| Cellulose ester | 20–37.5 |
| Plasticizer (lower molecular weight) | 0.1–6.5 |
| COATING C | |
| First water soluble polymer | 0.5–5 |
| First opaquant | 0.1–10 |
| Second opaquant | 1.0–15 |
| Colorant | 0.001–0.05 |
| COATING D | |
| Risperidone | 0.25–20 |
| Filler | 280–500 |
| Binder | 15–60 |
| Disintegrant | 12–70 |
| Glidant | 0.1–9 |
| Lubricant | 0.5–12 |

-continued

| INGREDIENT | Amount (mg) |
|---|---|
| COATING E | |
| Second water soluble polymer | 8–30 |
| Plasticizer (higher molecular weight) | 0.5–8 |
| Opaquant | 2–10 |
| Colorant | 0.01–0.05 |

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. A controlled release dosage form comprising a first composition comprising a therapeutically effective amount of venlafaxine, and a second composition comprising a therapeutically effective amount of an anti-psychotic agent, wherein the dosage form provides a controlled release of venlafaxine and an immediate release of the anti-psychotic agent, and wherein at least 75% of the anti-psychotic agent is released within about 1 hour after exposure of the dosage form to an aqueous solution, and at least 60% of the venlafaxine is released in a controlled manner within about 10 hours after exposure of the dosage form to an aqueous solution.

2. The dosage form of claim 1, wherein the release of at least one of the venlafaxine and the anti-psychotic agent has a delayed onset.

3. The dosage form of claim 1, wherein the dosage form delivers the anti-psychotic agent to the upper GI tract and the venlafaxine to the middle to lower GI tract of an animal to which it is administered orally.

4. The dosage form of claim 1, wherein the dosage form provides a venlafaxine $C_{max}$ of about 17–23 ng/ml of plasma when administered orally to a mammal.

5. The dosage form of claim 4, wherein the dosage form provides a venlafaxine $T_{max}$ at about 7–11 hours after oral administration.

6. The dosage form of claim 1, wherein the dosage form provides a venlafaxine dissolution profile as follows when exposed to an aqueous environment:

| Time (h) | Released (%) | STD (%) |
|---|---|---|
| 1 | 7.2 | 1.3 |
| 3 | 23.6 | 0.5 |
| 5 | 43.3 | 2.1 |
| 7 | 59.0 | 2.3 |
| 9 | 69.7 | 2.1 |
| 11 | 77.0 | 1.8 |
| 13 | 81.8 | 1.7 |
| 15 | 84.7 | 1.7 |
| 19 | 88.1 | 1.4 |
| 23 | ≥90.8 | 1.5. |

7. The dosage form of claim 1, wherein the dosage form provides a venlafaxine $C_{max}$ of about 20–27 ng/ml of plasma when administered orally to a mammal.

8. The dosage form of claim 7, wherein the dosage form provides a venlafaxine $T_{max}$ at about 3.5–8.5 hours after oral administration.

9. The osmotic device of claim 1, wherein the dosage form provides a single-dose venlafaxine plasma concentration profile in a mammal as follows:

| Time (h) | Mean VFX Plasma Concentration (ng/ml) | S.E.M. |
| --- | --- | --- |
| 0 | 0.0 | 0.0 |
| 0.5 | 0.3 | 0.2 |
| 1 | 0.4 | 0.2 |
| 2 | 3.2 | 0.8 |
| 4 | 13.9 | 2.6 |
| 6 | 17.5 | 2.5 |
| 8 | 18.7 | 2.7 |
| 10 | 18.8 | 2.9 |
| 12 | 16.7 | 2.5 |
| 14 | 15.8 | 2.7 |
| 16 | 11.8 | 2.0 |
| 20 | 8.6 | 1.7 |
| 24 | 6.6 | 1.1 |
| 28 | 5.7 | 1.5 |
| 32 | 3.4 | 0.7 |
| 36 | 2.2 | 0.5 |
| 48 | 1.7 | 0.5. |

10. The osmotic device of claim 1, wherein the osmotic device provides a single-dose venlafaxine plasma concentration profile in a mammal as follows:

| Time (h) | Mean VFX Plasma Concentration (ng/ml) | S.E.M. |
| --- | --- | --- |
| 0 | 0 | 0 |
| 0.5 | 0.2 | 0.2 |
| 1 | 1 | 0.4 |
| 2 | 6 | 1.6 |
| 4 | 21.2 | 3.1 |
| 6 | 22.6 | 3.3 |
| 8 | 21.3 | 4.0 |
| 10 | 16.8 | 2.9 |
| 12 | 15.4 | 3.3 |
| 14 | 13.4 | 2.8 |
| 16 | 9.6 | 1.5 |
| 20 | 8.9 | 2.5 |
| 24 | 6.5 | 1.5 |
| 28 | 4.6 | 1.1 |
| 32 | 3.7 | 1.0 |
| 36 | 3.1 | 0.9. |

11. The dosage form of any one of claims 1, or 2–10, wherein the anti-psychotic agent is selected from the group consisting of risperidone, olanzapine, clozapine, sertindole, ziprasidone, quetiapine, sulpiride, pimozide, clothiapine, molindone, loxapine, trifluoperazine, haloperidol, flupenthixol, chlorpromazine, chlorprothixene, clopenthixol, droperidol, perphenazine, fluphenazine, lithium, mesoridazine, spiperone, promazine, prochlorperazine, thioridazine, thiothixene, triflupromazine and raclopride.

12. A controlled release dosage form comprising a first composition comprising a therapeutically effective amount of venlafaxine, and a second composition comprising a therapeutically effective amount of an anti-psychotic agent, wherein the dosage form provides a controlled release of venlafaxine and an immediate release of the anti-psychotic agent;
at least 60% of the venlafaxine is released in a controlled manner within about 10 hours after exposure of the dosage form to an aqueous solution;
at least 75% of the anti-psychotic agent is released within about 1 hour after exposure of the dosage form to an aqueous solution; and
the release of at least one of the venlafaxine and the anti-psychotic agent has a delayed onset.

13. The dosage form of claim 12, wherein the dosage form delivers the anti-psychotic agent to the upper GI tract and the venlafaxine to the middle to lower GI tract.

14. The dosage form of claim 12, wherein the dosage form provides a venlafaxine $C_{max}$ of about 17–23 ng/ml of plasma when administered to a mammal.

15. The dosage form of claim 14, wherein the dosage form provides a venlafaxine $T_{max}$ at about 7–11 hours after administration.

16. The dosage form of claim 12, wherein the dosage form provides a venlafaxine $C_{max}$ of about 20–27 ng/ml of plasma when administered to a mammal.

17. The dosage form of claim 16, wherein the dosage form provides a venlafaxine $T_{max}$ at about 3.5–8.5 hours after administration.

18. The dosage form of any one of claims 12,13–17, wherein the anti-psychotic agent is selected from the group consisting of risperidone, olanzapine, clozapine, sertindole, ziprasidone, quetiapine, sulpiride, pimozide, clothiapine, molindone, loxapine, trifluoperazine, haloperidol, flupenthixol, chlorpromazine, chlorprothixene, clopenthixol, droperidol, perphenazine, fluphenazine, lithium, mesoridazine, spiperone, promazine, prochlorperazine, thioridazine, thiothixene, triflupromazine and raclopride.

19. A controlled release dosage form comprising a first composition comprising a therapeutically effective amount of venlafaxine, and a second composition comprising a therapeutically effective amount of an anti-psychotic agent, wherein the dosage form provides a controlled release of venlafaxine and an immediate release of the anti-psychotic agent;
at least 60% of the venlafaxine is released in a controlled manner within about 10 hours after exposure of the dosage form to an aqueous solution;
at least 75% of the anti-psychotic agent is released within about 1 hour after exposure of the dosage form to an aqueous solution;
the release of at least one of the venlafaxine and the anti-psychotic agent has a delayed onset; and
the dosage form provides a venlafaxine $C_{max}$ of about 17–23 ng/ml of plasma when administered to a mammal.

20. The dosage form of claim 19, wherein the dosage form provides a venlafaxine $T_{max}$ about 7–11 hours after administration.

21. A controlled release dosage form comprising a first composition comprising a therapeutically effective amount of venlafaxine, and a second composition comprising a therapeutically effective amount of an anti-psychotic agent, wherein the dosage form provides a controlled release of venlafaxine and an immediate release of the anti-psychotic agent;
at least 60% of the venlafaxine is released in a controlled manner within about 10 hours after exposure of the dosage form to an aqueous solution;
at least 75% of the anti-psychotic agent is released within about 1 hour after exposure of the dosage form to an aqueous solution;
the release of at least one of the venlafaxine and the anti-psychotic agent has a delayed onset; and the dosage form provides a venlafaxine $C_{max}$ of about 20–27 ng/ml of plasma when administered to a mammal.

22. The dosage form of claim 21, wherein the dosage form provides a venlafaxine $T_{max}$ about 3.5–8.5 hours after administration.

23. The dosage form of any one of claims 19–22, wherein the anti-psychotic agent is selected from the group consisting of risperidone, olanzapine, clozapine, sertindole, ziprasidone, quetiapine, sulpiride, pimozide, clothiapine, molindone, loxapine, trifluoperazine, haloperidol, flupenthixol, chlorpromazine, chlorprothixene, clopenthixol, droperidol, perphenazine, fluphenazine, lithium, mesoridazine, spiperone, promazine, prochlorperazine, thioridazine, thiothixene, triflupromazine and raclopride.

* * * * *

UNITED STATES PATENT AND TRADEMARK OFFICE
CERTIFICATE OF CORRECTION

PATENT NO. : 6,572,890 B2
DATED : June 3, 2003
INVENTOR(S) : Joaquina Faour et al.

It is certified that error appears in the above-identified patent and that said Letters Patent is hereby corrected as shown below:

Column 21,
Lines 1 and 24, replace the phrase "osmotic device" with the phrase -- dosage form --.

Signed and Sealed this

Twenty-sixth Day of July, 2005

JON W. DUDAS
*Director of the United States Patent and Trademark Office*